United States Patent
Vom et al.

(10) Patent No.: US 9,234,823 B2
(45) Date of Patent: Jan. 12, 2016

(54) METHOD AND APPARATUS FOR HANDLING TISSUE SAMPLES

(75) Inventors: Eduardo Vom, Brunswick East (AU); Chester John Henderson, Preston (AU); Neville John Farmer, McLeod (AU)

(73) Assignee: LEICA BIOSYSTEMS MELBOURNE PTY LTD, Mount Waverly, Vic (AU)

( * ) Notice: Subject to any disclaimer, the term of this patent is extended or adjusted under 35 U.S.C. 154(b) by 1354 days.

(21) Appl. No.: 12/066,013

(22) PCT Filed: Sep. 6, 2006

(86) PCT No.: PCT/AU2006/001304
§ 371 (c)(1),
(2), (4) Date: May 29, 2008

(87) PCT Pub. No.: WO2007/028202
PCT Pub. Date: Mar. 15, 2007

(65) Prior Publication Data
US 2008/0254504 A1    Oct. 16, 2008

(30) Foreign Application Priority Data
Sep. 6, 2005   (AU) ............................... 2005904860

(51) Int. Cl.
*G01N 1/36* (2006.01)
*G01N 1/31* (2006.01)
*G01N 1/44* (2006.01)

(52) U.S. Cl.
CPC ... *G01N 1/36* (2013.01); *G01N 1/44* (2013.01)

(58) Field of Classification Search
CPC ... G01N 1/36; G01N 1/286; G01N 2001/315; A61B 10/0096
See application file for complete search history.

(56) References Cited

U.S. PATENT DOCUMENTS

| | | | |
|---|---|---|---|
| 5,817,032 A * | 10/1998 | Williamson et al. | 600/562 |
| 7,005,110 B2 | 2/2006 | Taft | |
| 2005/0112034 A1 * | 5/2005 | McCormick | 422/102 |

FOREIGN PATENT DOCUMENTS

| | | |
|---|---|---|
| DE | 4400815 A1 | 7/1995 |
| JP | 3-10245 | 1/1991 |
| JP | 3-68866 A | 3/1991 |
| JP | 10246691 A | 9/1998 |
| JP | 2000266744 A | 9/2000 |
| JP | 2003215004 A | 7/2003 |
| JP | 2004279243 A | 10/2004 |
| WO | 01/44784 A1 | 6/2001 |

OTHER PUBLICATIONS

Partial English Translation of Japanese Office Action dated Apr. 24, 2012, issued in corresponding Japanese Patent Application No. 2008-529419.
Partial English Translation of Japanese Office Action dated Sep. 27, 2011, issued in corresponding Japanese Patent Application No. 2008-529419.
Banker, A.S., et al., "The Agar sandwich technique for retinal biopsy processing", PubMed [online: www.pubmed.gov], Retina 16(6):530-4, [retrieved on Jan. 31, 2006]. Retrieved from the Internet: <URL: http:/www.ncbi.nim.nih.gov/entrez/query.fcgi?cmd=Retrieve &db=PubMed&list_uids=9002138&dopt=Abstract.
Janisch, R., "Orientated embedding of single-cell organisms", Stain Technology, vol. 49, No. 2, pp. 157-160, 1974, USA, by The Williams and Wilkins Co.
Van Der Wal, U.P. et al, "A method for the orientation of small and delicate objects in embedding media for light and electron microscopy", Stain Technology, vol. 53, pp. 56-58, 1978 USA, by The Williams and Wilkins Co.
Blewitt, E.S., et al, "Double embedding in agar/paraffin wax as an aid to orientation of mucosal biopsies", Journal of Clinical Pathology, vol. 35(3), p. 365, Mar. 1982.
Arnolds, W.J.A., "Orientated embedding of small objects in agar-paraffin, with reference marks for small section reconstruction", Stain Technology, vol. 53, No. 5, pp. 287-288,1978, USA, by The Williams and Wilkins Co.
ProSciTech: Sticky Tabs: p. 13: Labels, Adhesive/Conductive Tapes; Tabs, Wax & Parafilm, ProSciTech [online] [retrieved on Jan. 23, 2006]. Retrieved from the Internet: <URL: http:/www.proscitech.com.au/catalogue/i3.asp> and R4: Histology Cassettes, Base Moulds, Biopsy Foam Pads & Cassette Storage [online], [retrieved on Oct. 11, 2006]. Retrieved from the internet: <URL:http://www.proscitech.com.au/catalogue/r4.asp#RCAS-02>.
Ellis, R.C., et al., "The microtome: function and design", Woods and Ellis 2000 [online], [retrieved on Jan. 23, 2006]. Retrieved from the Internet:<URL: http:/www.home.primus.com.au/royellis/microt/microt.htm. See p. 10 first para, p. 14 top two paras.
Winsor, L., "Tissue processing", Woods and Ellis 2000 [online], [retrieved on Jan. 23, 2006]. Retrieved from the Internet: <URL: http:/www.home.primus.com.au/royellis/tp/tp.htm. See pp. 1, 13, 15, 16 and 22.
GENEQ catalogues: Histology—pp. 48-61 [online], [retrieved on Jan. 23, 2006]. Retrieved from the Internet: <URL: http:/www.geneq.ca/pdf%20biotech/histology.pdf. See p. 55 and 57. And 2006/2007 Laboratory & Research Instruments Catalogue [online], [retrieved on Oct. 11, 2006]. Retrieved from the Internet: <URL: http://www.geneq.ca/pdf_biotech2006/bio2006catal.pdf. See p. 92.

* cited by examiner

*Primary Examiner* — Maria Leavitt
*Assistant Examiner* — Kimberly A Aron
(74) *Attorney, Agent, or Firm* — Sughrue Mion, PLLC (57) ABSTRACT

A tissue handling apparatus is provided comprising a support and a locator, for processing and embedding tissue samples. The support and cover form a chamber, within which a tissue sample is oriented prior to processing. After processing, the tissue sample within the chamber is embedded and the locator is removed, leaving the tissue sample correctly oriented in embedding material, mounted to a support, ready for microtoming.

11 Claims, 8 Drawing Sheets

METHOD AND APPARATUS FOR HANDLING TISSUE SAMPLES

RELATED APPLICATIONS

This application is a U.S. National Phase Application under 35 U.S.C. 371 of International Application No. PCT/AU2006/001304, filed 6 Sep. 2006, which claims priority to Australian Provisional Patent Application No. 2005904860, filed 6 Sep. 2005, the entire contents of which are incorporated herein by reference.

FIELD OF INVENTION

The present invention relates to the handling of biological tissue samples. In particular, the present invention relates to a system for handling tissue samples for analysis. In one form the present invention relates to a method and/or apparatus for handling tissue samples for histological and/or pathological laboratory analysis involving preparation procedures such as, tissue processing and embedding.

BACKGROUND OF INVENTION

In general, the term "tissue handling procedure" can be used to describe procedures for preparing tissue samples for microscopic examination and, traditionally, comprises embedding the tissue sample in paraffin wax and sectioning the paraffin-embedded tissue sample very thinly with a microtome. Thereafter, the thin sections may be floated onto glass slides, stained and finally coverslipped for microscopic examination. In histopathology, not only are the size and shape of the cells considered, but also the tissue structure. It is therefore useful to orient the tissue properly so that the plane of cutting by the microtome produces a cross section of tissue suitable for examination. Prior to embedding, the tissue sample may undergo tissue processing in a tissue processor, in which the sample is processed with various fluid materials appropriate to assist in preparing the sample for the examination. In a typical tissue processing operation the tissue sample may be fixed, dehydrated, cleared, and then infiltrated with molten paraffin wax. Then, depending on the examination to be conducted and subsequent to embedding and sectioning, the tissue sample may be stained for a particular analysis methodology. The fluid materials used in tissue processing steps may comprise formaldehyde, alcohol, xylene or other solvents, and paraffin wax. In recent developments being the subject of co-pending patent applications by the present applicant, xylene-free processing is now possible.

Therefore, the term "tissue handling procedure" is used herein to refer to any one of the abovementioned procedures that are performed in preparing tissue samples for examination.

A histology laboratory processes a number of tissue samples for examination and it is important that the tissue samples be prepared as efficiently as possible.

For example, U.S. Pat. No. 3,674,396 to McCormick discloses cassettes in which a tissue sample is both prepared for embedding through exposure to various solutions and is then embedded in proximity to the cassette. The '396 McCormick patent discloses a process wherein the tissue sample is statically exposed to the various fluids required for preparation of the tissue samples. In the cassettes of the '396 McCormick patent, perforated walls are used to enclose the tissue samples while providing access to the tissue samples for the various solutions and finally to molten paraffin wax. After subjecting the tissue sample to the various tissue processing fluids, molten embedding material may be poured into the well of a mold. The treated tissue sample may then be removed from the cassette and oriented in a specific manner in the embedding material in the well of the mold. Typically the mold is then placed onto a cold surface to harden the bottom layer of embedding material to ensure the tissue stays in the correct orientation, before applying further embedding material to fully embed the tissue. Additional molten embedding material is then poured over the tissue sample. The cassette used to process the tissue sample is then placed over the well in the mold and additional molten embedding material is poured into the cassette. After the embedding material solidifies, a cast block is formed that comprises the cassette as its base and a protruding portion having the tissue specimen disposed adjacent its front surface. The size of various cassettes, which have been developed for processing tissue samples, has been relatively standardized so that the cassette may be used, inter alia, to clamp the block into a microtome for sectioning. U.S. Pat. No. 5,080,869 to McCormick describes a typical cassette presently used for processing tissue samples. The cassette of the '869 McCormick patent is stackable and may be used for preparing a plurality of specimens. The cassette generally comprises a plurality of apertures disposed in the walls of the cassette for passage of processing fluids in a direction both orthogonal and parallel to the plane of the bottom wall of the cassette. The cassette also comprises a sloping extension of the front wall of the cassette for ease in placing indicia on the cassette for identification of the sample.

In the majority of histology laboratories, tissue samples are processed in a cassette that has come to be manufactured in accordance with at least one de facto industry standard, for example, along the lines of the above noted '396 McCormick patent and thereafter the above noted '869 McCormick patent. One cassette is typically used per tissue sample in order to ensure samples may be uniquely identified and labelled to ensure accurate diagnosis. For diagnostic reasons samples may vary greatly in size, from samples that almost fill a cassette completely to small biopsies that may be less than 1 mm in diameter. With respect to prior art tissue cassettes, the tissue specimen is held loosely and individually in a cassette to segregate it from other samples. After tissue processing, the next step is usually embedding the tissue sample in paraffin wax. The embedding procedure typically comprises the following steps:

Specimen is taken out of the cassette at some time after tissue processing is completed;

The histologist selects the correct size mold to use;

A small volume of wax is dispensed to the bottom of the mold;

The tissue specimen is placed into the mold and orientated carefully by the laboratory technician using wax to orient the tissue;

A holding fixture for the microtome (ordinarily a portion of a tissue cassette) is placed on the top of the mold. The fixture also provides an identification label;

Additional wax is dispensed by the technician to attach the fixture to the tissue sample, now enclosed in a block of wax;

The wax block is then cooled and solidified;

The wax block is then removed from the mold and ready to be mounted on the microtome via the fixture for sectioning.

The above procedure requires the histologist to spend time removing the tissue from the cassette after tissue processing and then orienting the samples in wax in their own mold.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein or, any claims defined herein.

SUMMARY OF INVENTION

In one embodiment, a method of handling a tissue sample comprises the steps of applying an orienting material to a tissue locator, placing a tissue sample on the tissue locator, orienting the tissue sample with respect to the tissue locator using the orienting material, applying a tissue handling procedure to the tissue sample in an oriented position.

In one form, the step of applying an orienting material to the tissue locator comprises applying a thin layer of orienting material to a surface of the locator.

In one form the method comprises the step of activating the orienting material after orienting the tissue sample. This allows the tissue to be oriented easily, but once activated, the tissue, will remain in place during a handling procedure such as tissue processing.

In another embodiment, a tissue handling apparatus comprises a tissue support, a tissue locator, and adapted for applying an orienting material on a surface of the locator, wherein a chamber is formed between the support and the locator, such that an orienting material on the surface of the locator is substantially within the chamber.

In one form the locator has a number of keying elements to assist the adhesion of a tissue sample to the surface of the locator.

In one form the keying elements are apertures in the locator. In one form the surface of the locator has one or more fluid flow paths. The fluid flow paths may aid in processing of the tissue in a tissue processor.

In one form the tissue handling apparatus comprises a member to block the flow of fluid through the fluid flow paths. In one form the member is detachable from the tissue handling apparatus. In one other form the member may be moved from a position where the fluid flow paths are open, to a position where the fluid flow paths are closed. This allows fluid flow through the tissue handling apparatus when the fluid flow paths are opens assisting tissue processing, and restricts fluid flow through the tissue handling apparatus when embedding the tissue.

In another aspect, a tissue sample handling apparatus comprises:

a first member having a supporting surface structure adapted to cooperate with an orientating medium for affixing a tissue sample relative to the surface in a predetermined orientation and wherein at least a portion of the sample handling apparatus comprises an asymmetric cross section for determining the orientation of a tissue sample disposed on the surface.

In a further aspect, a method of tissue handling comprises the steps of:

binding a tissue sample to a locator using an orienting material forming a processing chamber between the locator and a support processing the tissue sample embedding the tissue sample separating the locator from the support.

In yet another aspect a method of disposing a tissue sample at a supporting surface for enabling at least one tissue handling procedure is disclosed, the method comprising the steps of:

applying an orientating medium to the surface;

applying the tissue sample to the orientating medium such that the tissue sample is affixed relative to the surface in a predetermined orientation;

applying at least one step of a tissue handling procedure to the affixed tissue sample.

In yet a further aspect, a method of disposing a tissue sample at a supporting surface for enabling at least one tissue handling procedure is disclosed, the method comprising the steps of:

applying the tissue sample to the surface;

applying an orientating medium to the surface such that the tissue sample is affixed relative to the surface in a predetermined orientation;

applying at least one step of a tissue handling procedure to the affixed tissue sample.

BRIEF DESCRIPTION OF THE DRAWINGS

Further disclosure, objects, advantages and aspects of the present application may be better understood by those skilled in the relevant art by reference to the following description of embodiments taken in conjunction with the accompanying drawings, which are given by way of illustration only, and thus are not limiting to the scope of the present invention, and in which:

FIG. 11b shows a schematic representation of a cross section of an embedded tissue sample separated from the locator and orienting medium of FIG. 11a;

FIG. 12b shows a schematic representation of a cross section of an embedded tissue sample separated from the locator and orienting medium of FIG. 12a;

DETAILED DESCRIPTION

Figure 1:
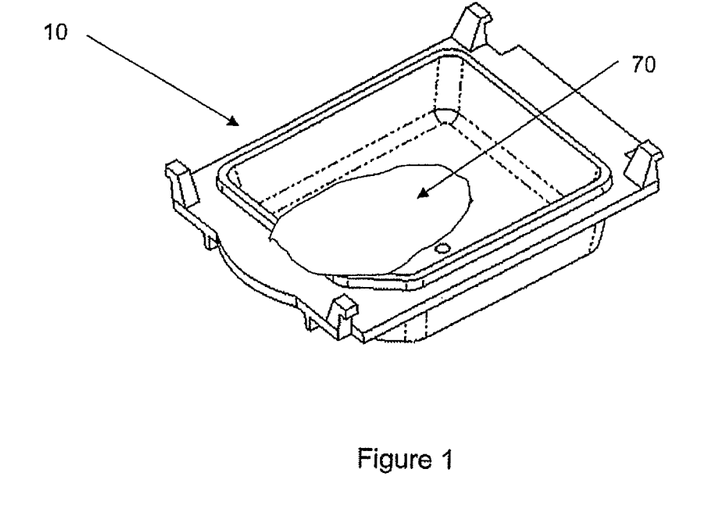
FIG. 1 shows a perspective view of a first embodiment of a locator apparatus and an orientating medium applied to the surface thereof.
Figure 2:
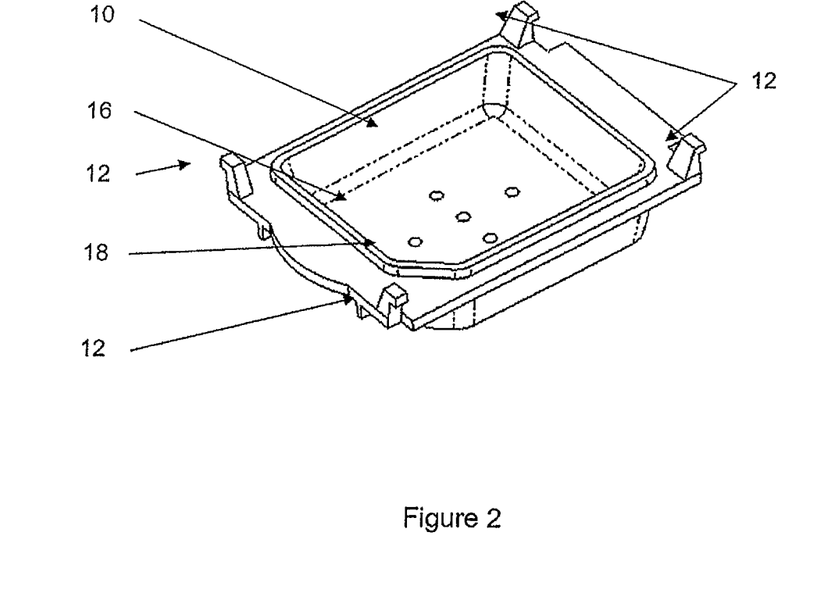
FIG. 2 shows a perspective view of a second embodiment of a locator apparatus.
Figure 3:
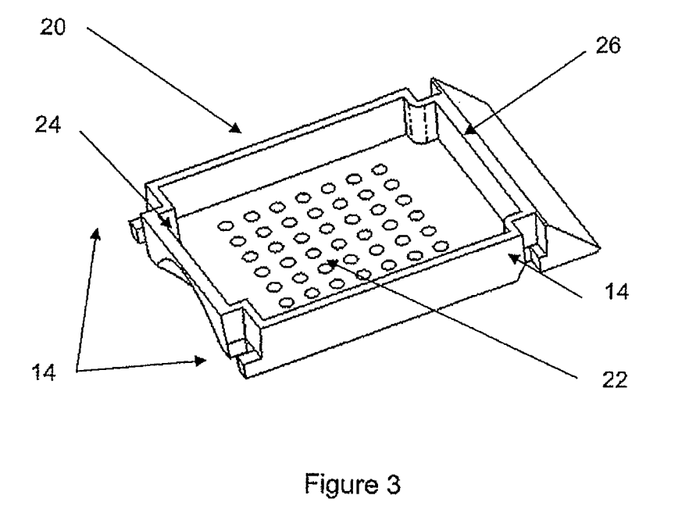
FIG. 3 shows a perspective view of a first embodiment of a support device.

With reference to the drawings there is shown two parts of a tissue handling tissue handling apparatus, comprising a tissue locator 10, shown in FIGS. 1 and 2, and an embedding support 20 shown in FIG. 3. Tissue locator 10 and embedding support 20 are adapted to detachably fit together as shown in FIG. 4 to provide a processing chamber 30 (shown in FIG. 9c) which may contain one or more samples or pieces of tissue (not shown).

Tissue locator 10 is shown with a number of engagement devices, in this embodiment legs 12 adapted to engage corresponding recesses 14 in the embedding support 20. Other methods of attaching the locator to the support may be used.

Figure 4:
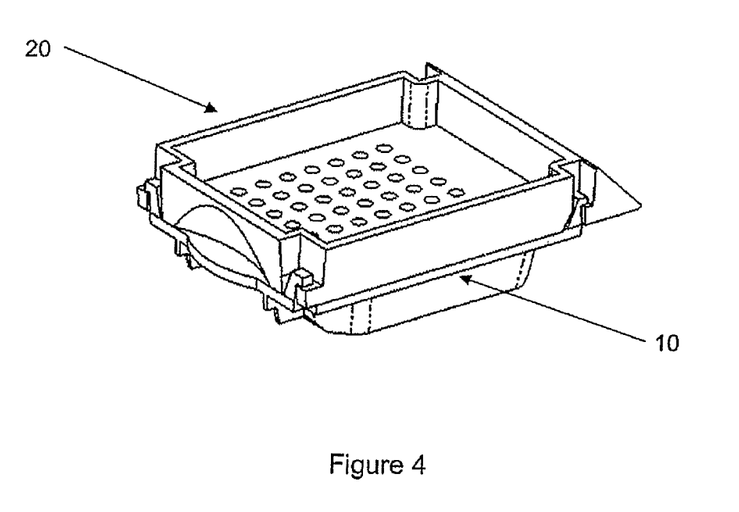
FIG. 4 shows a perspective view of the locator of FIG. 1 and support of FIG. 3.

In the arrangement in FIG. 4, a tissue sample may be located in the chamber for processing.

The locator 10 comprises a support surface 16, which in use would support a tissue sample (not shown). In the embodiment in FIG. 2, the support surface 16 comprises an engagement mechanism in the form of apertures 18 in the surface 16. The apertures 18 comprise one embodiment of fluid flow paths into the chamber 30.

The support 20 comprises apertures 22 in a base 24, and an identification surface 26 for identifying the tissue sample. In the present embodiment the support 20 is based on a tissue handling apparatus used for processing tissue in a tissue processor such as a Leica™ TP1050 or a Vision BioSystems Peloris™ tissue processing instrument.

Figure 5:
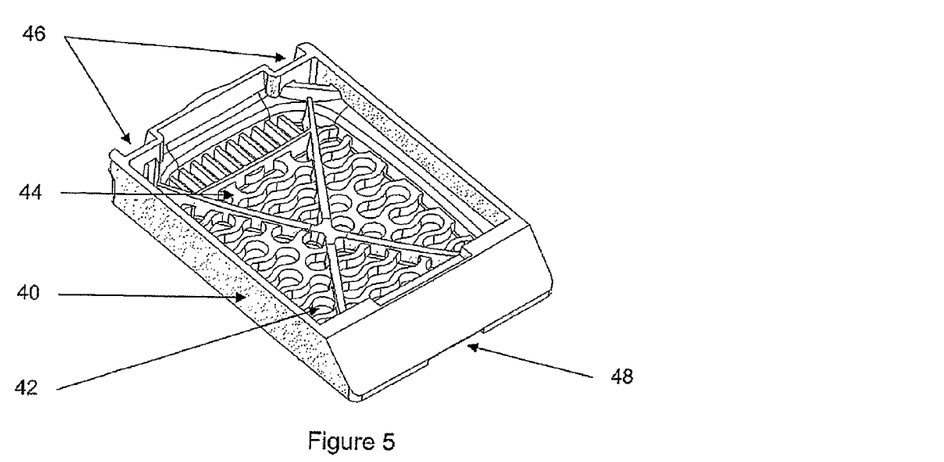
FIG. 5 shows a perspective view of a second embodiment of a support device.

In FIG. 5, embedding support 40 is shown, comprising apertures 42 in the base 44. Alternate locating mechanisms may also be used to attach a tissue locator to the embedding support 20, such as recesses 46 and 48.

Figure 6A:
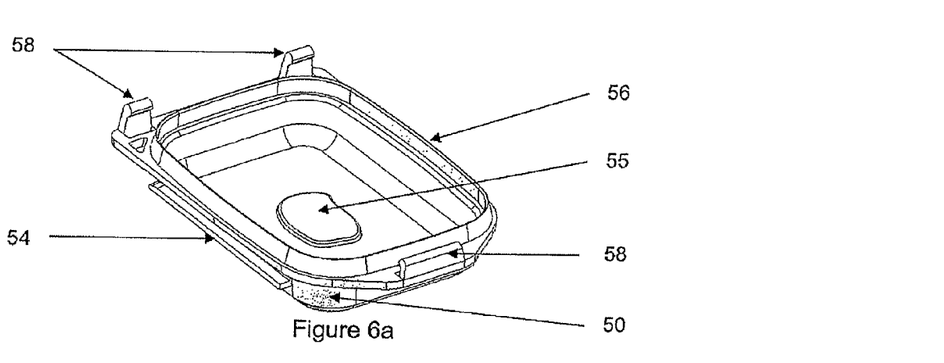
FIG. 6a shows a perspective view of a third embodiment of a locator apparatus and an orientating medium applied to the surface thereof.
Figure 6B:
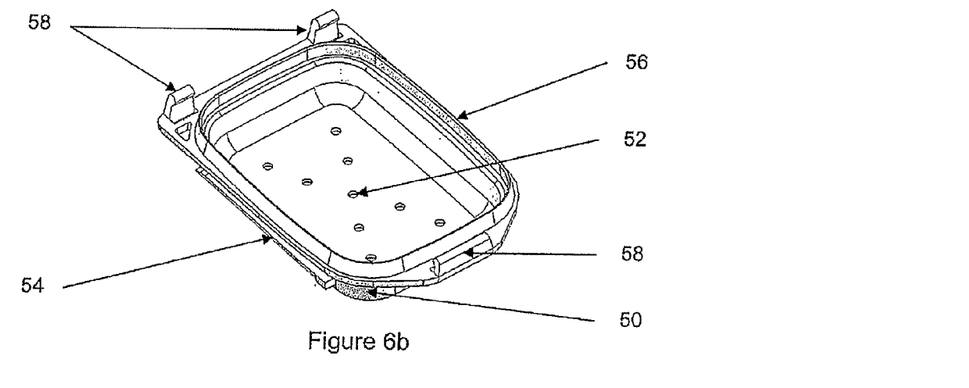
FIG. 6b shows a perspective view of a fourth embodiment of a locator apparatus.

FIGS. 6a and 6b show further embodiments of a tissue locator 50. The apertures 42 and 52 combine to allow flow of processing fluids through the chamber therebetween to assist in processing the tissue in a tissue processor. FIG. 6a shows a wall 56 which corresponds to a recess in the support 40 to form a chamber. The wall is shown without fluid flow paths, which is advantageous for the embedding step, but fluid flow paths may be present if additional fluid flow during processing is desired. Tabs 58 interact with recesses 46 and 48 to releasably hold the locator 40 to support 50.

As shown in FIGS. 1 and 6a, a material 70 or 55 respectively may be placed on the support surface of the locator. This material is used to locate a tissue sample (not shown) in a position, and in one form is used to locate the tissue sample in a specific orientation. The types of embedding material that may be used are described in co-pending application titled "Composition and Method for Handling Tissue Samples" filed on 5 Sep. 2006 by Vision BioSystems Ltd, the contents of which are incorporated by reference.

The orientating material for supporting a tissue sample in a predetermined orientation relative to a supporting surface of a tissue handling device may be a composition comprising a gelling agent and an organic solvent and wherein the composition is substantially liquid at room temperature.

In one embodiment, the gelling agent is a carbohydrate based polymer selected from the group comprising agarose, comprising agarose derivatives and modified agarose such as low melt agaroses, hydroxyethylagaroses and low molecular weight agaroses, agar, alginates and cellulose, comprising hydroxypropylcellulose, or combinations thereof.

Carbohydrate polymers have a high gel strength at relatively low solids content. This allows for compositions, based upon these polymers, to possess suitable mechanical strength to act as adhesives for tissue samples, but still offer little resistance to solvent exchange as they possess a very open and permeable structure due to their low solids content. In addition, carbohydrate polymers possess a strong affinity for tissue (animal and plant), which allows them to form around and adhere strongly to samples. Also, the strength of the bond of the carbohydrate polymer to the tissue handling device is sufficient that it reliably holds the tissue at the desired orientation throughout tissue handling procedures, but that the strength of the carbohydrate polymers attachment to the tissue handling device is such that it still releases from the tissue handling device when the embedded wax sample is separated from the surface of the tissue handling device on which it was orientated at the completion of the embedding process. Carbohydrate polymers in general have been found to be relatively non-reactive throughout tissue processing protocols. They also have a relatively low retention of the various dyes and stains used in the histological tissue handling protocols.

In a preferred embodiment, the gelling agent is present in an amount of about 0.1% (% w/v) to about 15% (% w/v). More preferably, the gelling agent is present in an amount of about 0.3% (% w/v) to about 10% (% w/v). Even more preferably, the gelling agent is present in an amount from about 1% (% w/v) to about 4% (% w/v).

In one embodiment, the organic solvent is a non-aqueous solvent selected from the group comprising ethanediol, 1,3-propanediol, glycerol, 1,2 propanediol, 1,2 butanediol, 1,3 butanediol, 1,4 butanediol, polyethylene glycols such as diethylene glycol, triethylene glycol, alcohols such as methanol, ethanol, dimethylformamide, formamide, dimethylsulfoxide or combinations thereof.

In a further embodiment, the orientating composition according to the present invention comprises an antimicrobial compound, stabilizer, preservative or combination thereof.

"Substantially liquid" as used herein with respect to orientating material comprises orientating compositions in a suitably viscous, pliable gel or paste-like form.

Figure 9A:
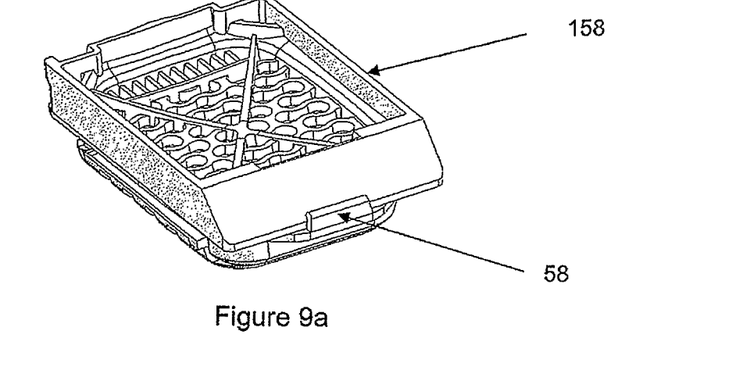
FIGS. 9a and 9b shows two perspective views of one embodiment of the assembly of FIG. 8.
Figure 9B:
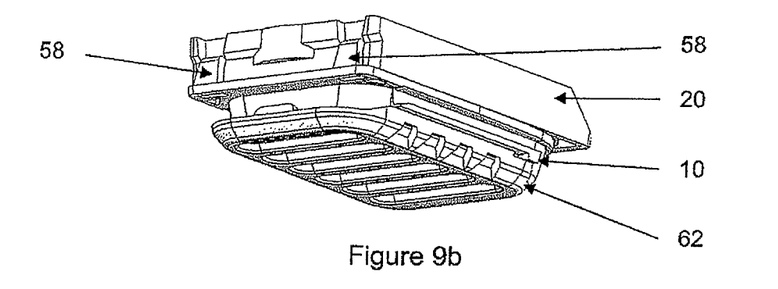
Figure 9C:
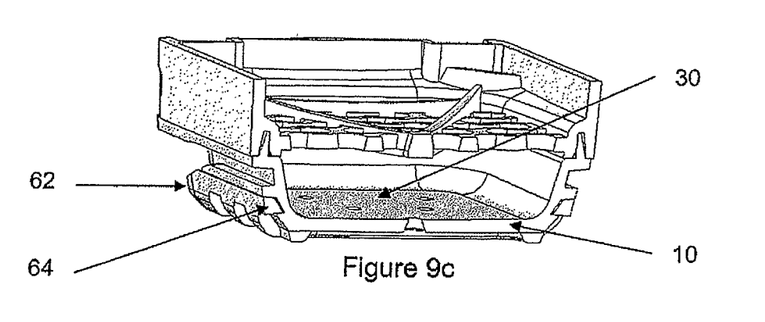
FIG. 9c shows a cross sectional perspective view of the assembly of FIGS. 9a and 9b.
Figure 10A:
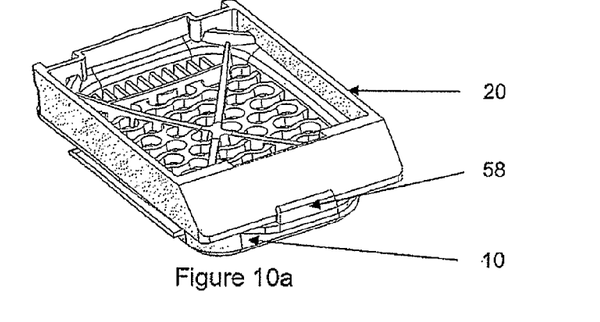
FIGS. 10a and 10b show two perspective views of a second embodiment of the assembly of FIG. 8.
Figure 10B:
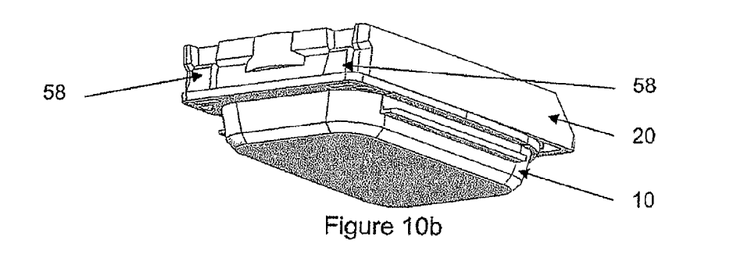

The orientating composition according to embodiments of the present invention is able to grip and/or mold to hold or adhere to the tissue and is sufficient to hold the appropriate orientation of the tissue through tissue handling procedures such as processing when employed at room temperature. Preferably the material is an adhesive that locates the tissue with respect to the locator, without covering a substantial portion of the tissue. As the tissue may be located and oriented within the chamber 30 prior to tissue handling procedures, for example tissue processing, it is preferable to allow the processing fluid to contact as much tissue as possible.

Further, the adhesive should preferably have one or more of the following properties:
  Sufficient hold to prevent the tissue sample changing orientation in any substantial way during processing;
  Sufficient initial tack to hold tissue in place but allow the tissue to be manipulated during placement to ensure the correct orientation can be achieved.

For example, it may be preferable to allow the tissue to be initially placed in contact with the material, then oriented correctly, then allow the material to increase its adhesion so that the tissue orientation does not substantially change during typical handling of the tissue handling apparatus prior to embedding.

In one form the material may increase its adhesion sometime after orientation in the chamber 30. Some examples of methods of accomplishing this are using a material that sets over time; a material that reacts with components in the tissue (for example water or formalin); a material that reacts with an additive placed onto the material after orientation, or a pressure sensitive adhesive.

Methods and configurations of orienting material on locators may include applying a liquid reagent as herein described directly to a locator then applying a tissue sample in the desired orientation. In another form the orienting material may be pre-applied. The pre-applied orienting material may be covered with the cover removed just prior to orienting the tissue, such that exposure to air or moisture in the air or tissue may promote gelling of the material, providing time to orient the tissue before gelling. In a further embodiment the orienting medium may be applied by a spray to the surface of the locator. In another embodiment the orienting material may be applied first to the tissue, then the tissue placed on the locator surface.

After processing, the tissue will be embedded. To embed the tissue, the tissue should be oriented, on the tissue support surface 16. In use, the tissue is placed onto the surface 16 of a locator such as locator 50. An orienting material 55 is used to enable the tissue to be oriented and located in place. In prior art cassettes, the tissue would be placed within a cassette, but not oriented. It would be processed, and then oriented after processing, either before or during embedding. Such a procedure required the tissue to be placed inside a cassette, processing of the tissue, then opening the cassette and orienting the tissue, typically using the embedding material to locate and orient the tissue in place. In the embodiments described herein, it is not necessary to orient the tissue after processing as the tissue is not initially oriented with respect to the support, but to the locator which is removable from the support. Thus, it is possible to orient the tissue with respect to a locator, attach a support in a known way to the locator, process the tissue, embed the tissue, separate the locator from the support with the embedded tissue staying on the support, and have the tissue oriented with respect to the support without the locator being in place. This becomes advantageous as the support may be configured to conform to a shape and size of known tissue cassettes that fit microtomes. With the support in place the tissue is held in a chamber. By removing the support the microtome can access the embedded tissue sample within the chamber to remove sections of embedded tissue.

Figure 12A:
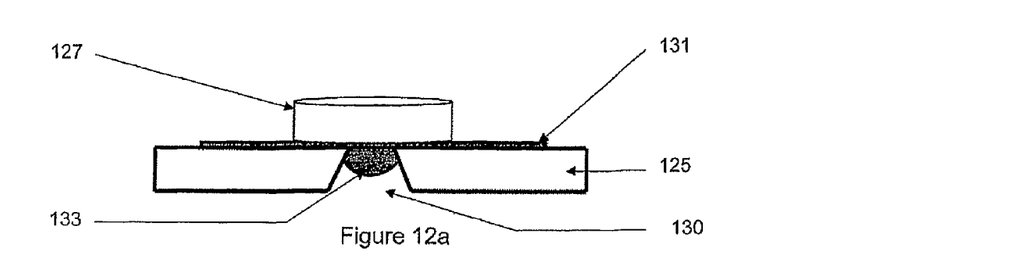
FIG. 12a shows a schematic representation of a cross section of a tissue sample oriented on a locator using a mechanically bonding orienting medium.
Figure 12B:
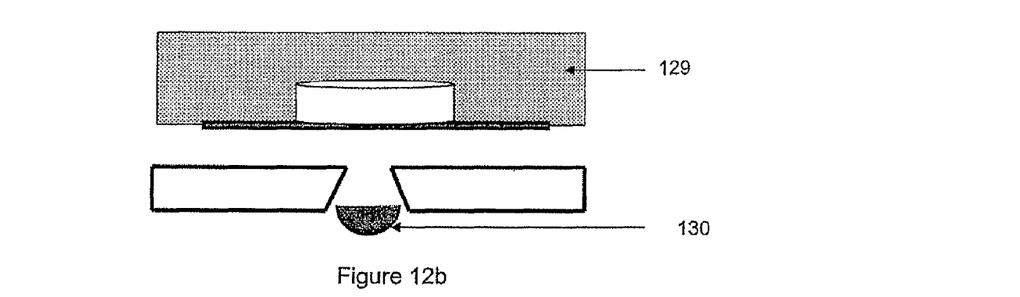
Figure 13A:
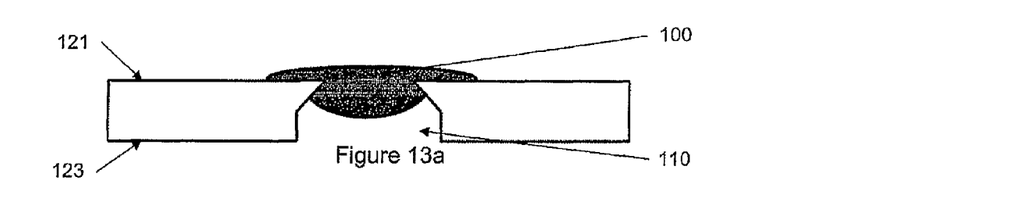
FIGS. 13a to 13g are schematic cross-sectional representations of an orientating medium on a locator having various embodiments of keying mechanisms.
Figure 13B:
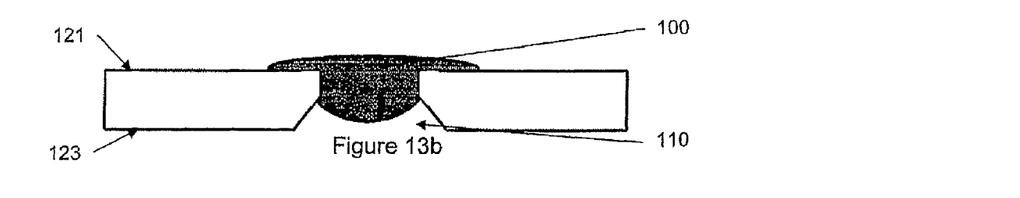
Figure 13C:
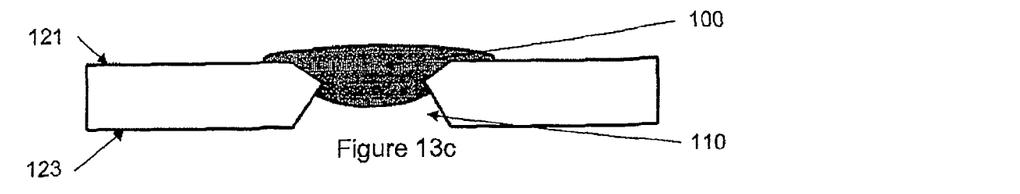
Figure 13D:
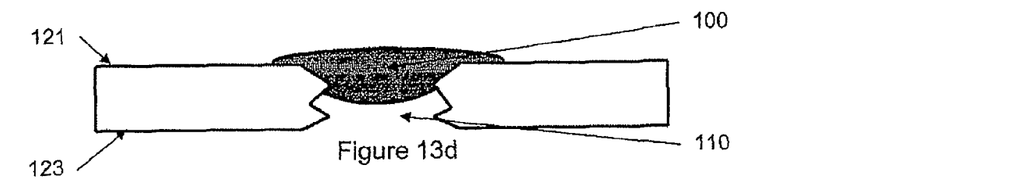
Figure 13E:
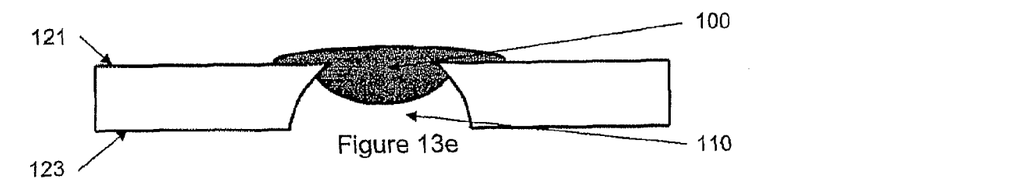
Figure 13F:
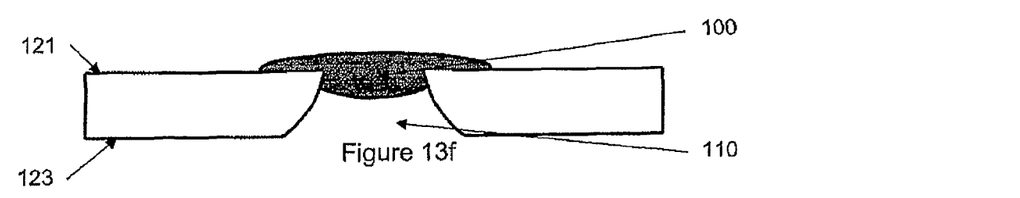
Figure 13G:
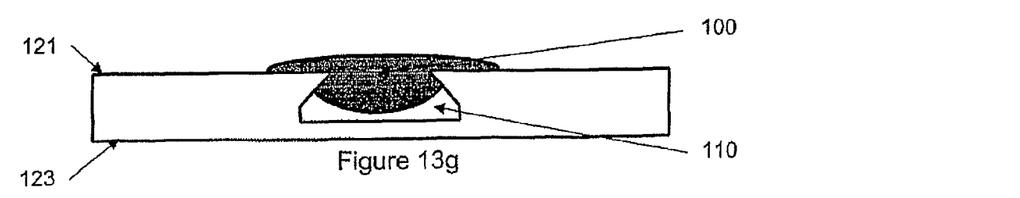

An example of the chamber is chamber 30 shown in FIG. 9c. It is not necessary to have apertures or fluid flow paths in both the locator and support or respective embodiments. Further, fluid flow paths may be present in the sidewalls of the locator or support FIG. 6a also shows orienting material 55 on the support 50. A tissue sample may be placed in the orienting material 55 for orientation. In FIG. 6b, apertures 52 are shown in the support 50, and the orienting material may interact with the apertures 52 as shown for example in FIGS. 13a to 13g. The apertures 52 may also be straight edged or in a variety of other configurations as well, including not fully perforating the locator surface as shown in FIG. 13g. In FIGS. 13a to 13f, the orienting material 100 is shown sinking into apertures 110. The degree of penetration of the orienting material 100 into the aperture 110 depends on the configuration of the aperture 110, the viscosity of the orienting material 100, time, temperature and other factors. The orienting material 100 can be configured to give an appropriate keying effect with the aperture to achieve sufficient grip with the support, such that the tissue remains oriented during processing, but once embedded, releases from the support to remain surrounded by embedding material such as paraffin wax, and substantially retains its orientation. An example of the method of mechanical keying of the orienting material on a locator is shown in FIG. 12a, where a tissue sample is oriented on a locator 125 using orienting material 131. While orienting material 131 is applied in this embodiment in a thin layer on the locator, some orienting material has gathered in the aperture 130 to form a key 133, mechanically assisting in preventing the tissue from moving. When the locator is released from the support, as shown in FIG. 12b, the key breaks away from the embedding material, releasing the tissue sample from the locator.

Figure 11A:
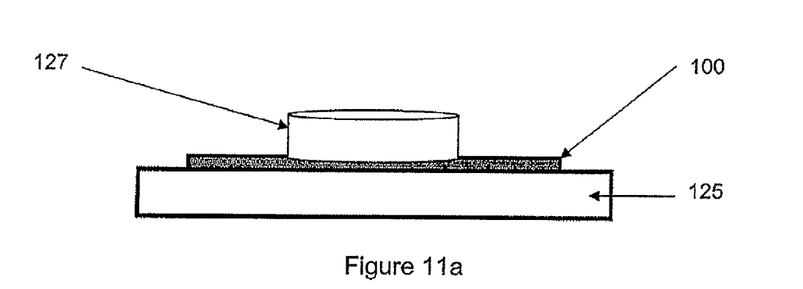
FIG. 11a shows a schematic representation of a cross section of a tissue sample oriented on a locator using a chemically bonding orienting medium.
Figure 11B:
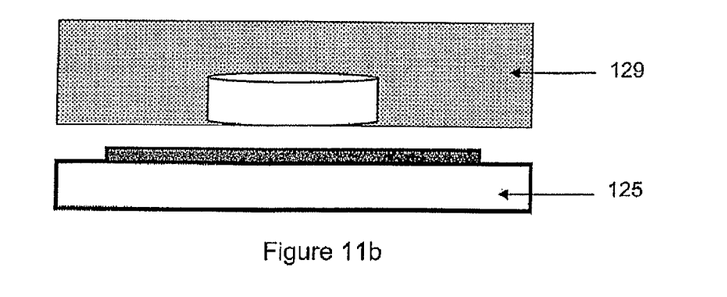

In another form, the orienting material may chemically bond with the locator. This process is shown in FIGS. 11a and 11b where tissue 127 is placed on a support surface 125, the surface 125 having a layer of orienting material 100. After processing the embedding material 129 attached to a support (not shown) is removed from the locator 125 and in this embodiment the orientating material 100 remains on the locator 125. In this case the orienting material may chemically interact with the material on the surface of the locator. Chemical interaction is common among adhesives, and various types of adhesive are mentioned in the abovementioned co-pending application incorporated by reference.

In other embodiments the orienting material 100 may remain partially or fully on the embedding material, or be separately removable from both locator and embedding material.

Figure 7:
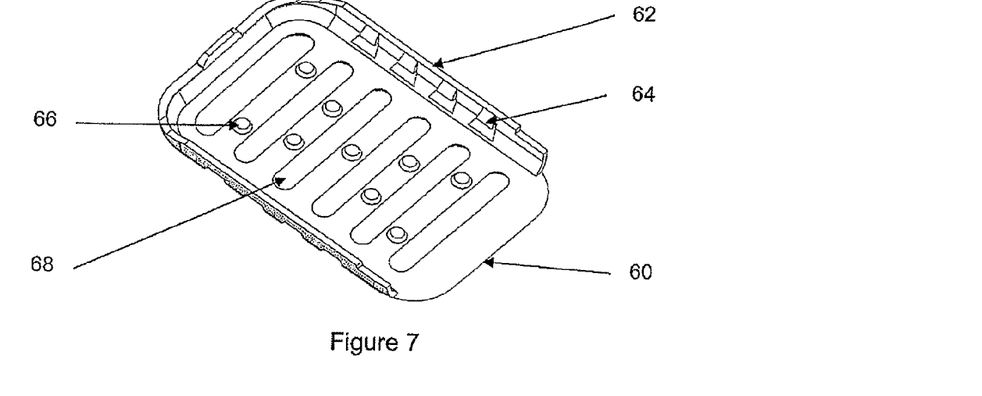
FIG. 7 shows a perspective view of a member adapted to fit the locator of FIG. 6b.
Figure 8:
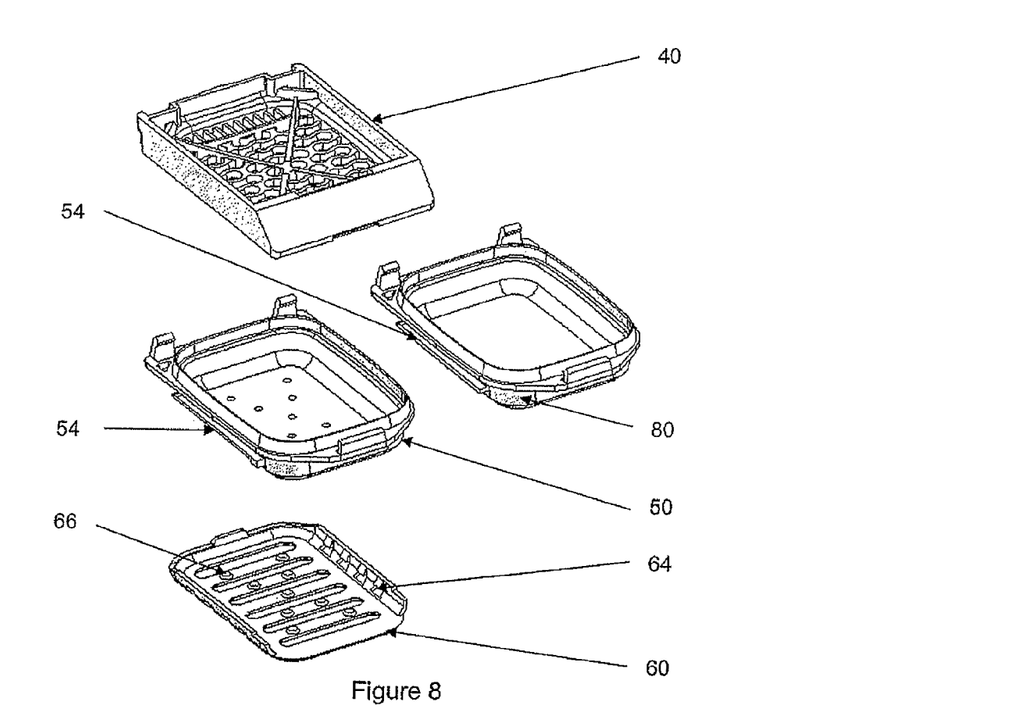
FIG. 8 shows an exploded perspective view of an assembly comprising the support of FIG. 5, locators of FIGS. 6a and 6b, and the member of FIG. 7.

After processing, the locator and support holding the tissue in the chamber may proceed to an embedding stage. The locator and support, for example as shown in FIG. 4, maybe placed under a dispenser for dispensing embedding material such as paraffin wax. The chamber is filled with paraffin wax through the apertures in the support. In order to assist in filling the chamber with wax, a member 60 may be supplied, as shown in FIGS. 7 and 8. Member 60 includes an engagement mechanism which in this case includes side rails 62 and projections 64. Projections 64 engage with corresponding grooves 54 on, for example, tissue locator 50, and allow the member 60 to move with respect to the locator 50 from a position where projections 66 correspond to apertures 52 in the locator (a closed position), to at least one second position where the projections 66 do not correspond, being an open position. The member may be completely removable as well.

In another embodiment (not shown), the apertures may be blocked by a plug that corresponds to the number and locations of the apertures, or a removable plate.

Prior to processing, the member 60 is in a position whereby the apertures are not blocked by the projections, that is they are out of alignment. Further, as can be seen in FIGS. 7, 8 and 9b, there are openings 68 in the member 60. The openings 68 correspond with the apertures when the member 60 is engaged with the locator 50 in a first position, which may be called an open position. The open position is useful in that it allows processing fluid to flow through the apertures in the locator 50 shown in FIG. 8, such as apertures 52 in FIG. 6b. In one example, the entire tissue handling apparatus 158, as shown in FIG. 9a, is placed into a tissue processor. The tissue handling apparatus 158 contains a pre-oriented tissue sample (not shown), and the member may be in an open position or a closed position. In an open position the apertures 42 in the support allow fluid in the tissue processor to flow through the chamber, increasing the effectiveness of the processing. The locator may also have apertures for fluid flow. The member 60 may not be attached to the locator during processing, which would also allow the fluid flow through apertures 42.

During embedding, it may be desirable to have no fluid flow paths from the locator, as the chamber 30 is to be filled with embedding fluid such as paraffin wax. Several methods may be used to prevent fluid leaking from the chamber such as:

using a locator without apertures;
  using a locator with apertures and plugging the apertures with a member such as member 60;
  using a fluid to block the apertures before applying the embedding fluid;
  using the embedding fluid to block the apertures.

In the case of paraffin wax, one embodiment is to place the locator and support attached together on a cold plate, applying a small amount of embedding fluid to the chamber to seal the apertures, then filling the chamber with wax.

In one form, the locator is supplied with a member that blocks the apertures in the locator. The tissue may then be warmed, for example by placing the locator and support on a warming plate to heat the tissue sample so that it is a similar temperature to the molten wax, for example 65 degrees Celsius. The paraffin wax is then applied to the warmed chamber until it is full. The locator and support may then be left to cool under ambient conditions or exposed to accelerated cooling such as a refrigerant or cold plate to solidify the wax. It has been found that heating the tissue sample before applying the wax improves the embedding of the tissue. Once the wax has solidified, the locator may be removed from the support, and the tissue will be embedded in a wax block attached to the support, that formed inside the chamber. The locator acts as a mold for the embedding material, and sufficient embedding material is usually put into the chamber so that the excess covers the apertures in the support and thereby binds to the support more strongly than the orienting material binds to the locator. In the same way as the apertures in the locator may be tapered or profiled to enhance mechanical keying with the surface, the apertures in the support may also be profiled or tapered to increase mechanical keying with the surface, to increase the likelihood of the embedding material and tissue separating from the surface of the locator and remaining in contact with the support.

While paraffin wax has been described as an embedding material, other commonly used embedding materials may be used.

The locator and support of the present invention are typically made from a plastics material. The locator, which interacts with the orienting material, may be a specific material, for example a plastic such as Acetal polyoxymethylene copolymer (POM), high-density polyethylene (HDPE) and polytetrafluoroethylene (PTFE—Teflon®—Dupont), to facilitate chemical or mechanical bonding of the orientating composition to the surface. The surface of the tissue handling device may comprise a further chemical, i.e. a coating of the aforementioned plastics, applied to a base plastic or metal, to provide the desired mechanical properties such as strength or heat transmission. Thus it is possible to use different material for different parts, for example the locator may be made from a metal so as to increase its heat transmission properties to assist in heating and cooling the tissue during embedding.

In this description only a single piece of tissue is described in each chamber. However, a number of pieces of tissue may be oriented on each locator, and other material may be oriented on the locator as well, such as a control substance or a guide material used in automated imaging.

A person skilled in the art will recognise that embodiments of the invention described herein may be implemented using one or more computers and/or computer or microprocessor controlled devices. In that case, the method steps disclosed herein may be embodied as instructions that comprise a computer program. The program may be stored on computer-readable media, such as floppy disks, optical discs (eg compact discs), or fixed disks (such as hard drives and the like), and may be resident in memory, such as, for example random access memory (RAM), read-only memory (ROM), firmware, or flash RAM memory. The program as software may then be executed on a computer or microprocessor device to implement the method. The program or portions of its execution, may also be distributed over multiple computers in a network having a topology corresponding to one or a combination of: a small area such as in a LAN (Local Area Network); a large campus or city area such as in a MAN (Metropolitan Area Network) or; a wide geographical area such as in a WAN (Wide Area Network).

While this invention has been described in connection with specific embodiments thereof, it will be understood that it is capable of further modification(s). This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The term tissue sample is intended to cover not only tissue biopsies from plants and animals, but also to cover congregations of cells from for example cell scrapings. For example, it is also envisaged that the present invention may be applied to tissue samples taken for cytological analysis.

It will be appreciated by persons skilled in the art that numerous variations and/or modifications may be made to the invention as shown in the specific embodiments without departing from the spirit or scope of the invention as broadly described. The presently described embodiments herein are, therefore, to be considered in all respects as illustrative and not restrictive.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention as described hereinabove. Therefore, the specific embodiments are to be understood to be illustrative of the many ways in which the principles of the present invention may be practiced. In the description hereinabove and claims hereinbelow, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The claims defining the invention are as follows:

1. A method of handling a tissue sample comprising:
applying an adhesive to a tissue locator of a tissue handling apparatus,
the tissue locator including an upper surface and a lower surface,
the tissue locator including a plurality of keying elements comprising apertures extending from the tissue locator upper surface into the tissue locator lower surface,
wherein said apertures assist the adhesion of a tissue sample to the upper surface of the locator,
wherein the apertures comprise a tapered cross-sectional profile from the tissue locator upper surface towards the tissue locator lower surface,
wherein the cross-section of an aperture at the tissue locator upper surface is smaller than a cross-section of the same aperture in the tissue locator, wherein the adhesive is applied so as to gather in the apertures to form a key, placing a tissue sample on the tissue locator, orienting the tissue sample with respect to the tissue locator using the adhesive, wherein the adhesive gathers in the apertures to form a key and mechanically assist in preventing the tissue from moving, and applying a tissue handling procedure to the tissue sample in an oriented and located position.

2. The method of claim 1, wherein the applying the adhesive to the tissue locator comprises applying a thin layer of adhesive to a surface of the locator.

3. The method of claim 1, further comprising attaching the tissue locator to a tissue support.

4. The method of claim 1, wherein the applying the tissue handling procedure to the tissue sample comprises embedding the sample in an embedding medium.

5. The method of claim 4, further comprising removing the tissue locator from the tissue support once the tissue has been embedded.

6. The method of claim 1, further comprising activating the adhesive after orienting the tissue sample.

7. A method of tissue sample handling comprising:
applying an orientating material and at least one tissue sample to a tissue locator of a tissue handling apparatus, the tissue locator including an upper surface and a lower surface,
the tissue locator having a plurality of apertures,
wherein the orientating material is applied so as to gather in the apertures and form a plurality of keys,
wherein the apertures comprise a tapered cross-sectional profile from the tissue locator upper surface towards the tissue locator lower surface,
wherein the cross-section of an aperture at the tissue locator upper surface is smaller than a cross-section of the same aperture in the tissue locator,
wherein the keys assist in affixing the tissue sample to the upper surface of the tissue locator,
wherein the orientating material is applied such that the tissue sample is affixed relative to the locator upper surface in a predetermined orientation, and
applying at least one step of a tissue handling procedure to the affixed tissue sample.

8. The method of claim 7, wherein applying the orientating material to the tissue locator surface comprises:
activating the orientating material; and
dispensing the activated orientating material onto the tissue locator surface such that the orientating material engages the tissue sample.

9. The method of claim 7, further comprising:
allowing the orientating material to set after the tissue sample has been affixed to the tissue locator surface.

10. The method of claim 7, wherein the applying the at least one step of the tissue handling procedure to the affixed tissue sample comprises one or more of:
applying a solution of about 10% formalin such that cross-links are formed in the orientating material thereby rendering the orientating material insoluble during subsequent steps of the tissue handling procedure and thereby ensuring the tissue sample remains affixed to the tissue locator upper surface during the subsequent steps of the tissue handling procedure; and
embedding the tissue sample.

11. A method of tissue handling comprising:
binding a tissue sample to a tissue locator of a tissue handling apparatus by using an orientating material to flow into a number of apertures located in the tissue locator, the tissue locator including an upper surface and a lower surface,
wherein the orientating material is configured and applied so as to gather in the apertures to form a plurality of keys, thereby binding the tissue sample to the tissue locator,
wherein the apertures comprise a tapered cross-sectional profile from the tissue locator upper surface towards the tissue locator lower surface,
wherein the cross-section of an aperture at the tissue locator upper surface is smaller than a cross-section of the same aperture in the tissue locator,
forming a processing chamber between the tissue locator and a support;
processing the tissue sample;
embedding the tissue sample; and
separating the tissue locator from the support.

* * * * *